United States Patent [19]
Dorsch et al.

[11] Patent Number: 5,321,045
[45] Date of Patent: Jun. 14, 1994

[54] METHOD AND COMPOSITION FOR THE TREATMENT OF IMFLAMMATORY CONDITIONS USING THIOSULPHINIC ACID DERIVATIVES

[75] Inventors: Walter Dorsch, Munich; Hildebert Wagner, Breitbrunn/Chiemsee, both of Fed. Rep. of Germany

[73] Assignee: Boehringer Mannheim GmbH, Mannheim, Fed. Rep. of Germany

[21] Appl. No.: 335,964

[22] PCT Filed: Jul. 12, 1988

[86] PCT No.: PCT/EP88/00628
§ 371 Date: Mar. 14, 1989
§ 102(e) Date: Mar. 14, 1989

[87] PCT Pub. No.: WO89/00422
PCT Pub. Date: Jan. 26, 1989

[30] Foreign Application Priority Data

Jul. 14, 1987 [DE] Fed. Rep. of Germany ....... 3723248

[51] Int. Cl.$^5$ ............................................. A61K 31/255
[52] U.S. Cl. .................... 514/518; 514/517; 514/825; 514/826
[58] Field of Search ............... 514/506, 707, 708, 517, 514/518, 825, 826; 560/310

[56] References Cited

U.S. PATENT DOCUMENTS 2,508,745  5/1950  Cavallito et al. .................. 260/453
3,686,324  8/1972  Brodnitz et al. ................... 260/453

FOREIGN PATENT DOCUMENTS 0153881  9/1985  European Pat. Off. .

OTHER PUBLICATIONS

Vanderhoek et al., Biochemical Pharmacology, 29, 1980, pp. 3169–3173.
Mohammed et al., Thrombosis Research, 44, 1986, pp. 793–806.
Harvard Health Letter, vol. 16, No. 7, May 1991, pp. 5–7.
New York Times Tuesday Mar. 26, 1991, C3.
American Health, May 1991, pp. 66–68 "Attacking Asthma".

*Primary Examiner*—Frederick E. Waddell
*Assistant Examiner*—Kimberly R. Jordan
*Attorney, Agent, or Firm*—Felfe & Lynch

[57] ABSTRACT

The invention concerns thiosulphinic acid derivatives, medicaments containing these compounds and their use in medicine. It has been found that thiosulphinic acid derivatives display outstanding inflammation-inhibiting properties. The compounds prove to be especially advantageous in the treatment of PAF-induced inflammatory processes of the bronchial area.

13 Claims, 6 Drawing Sheets

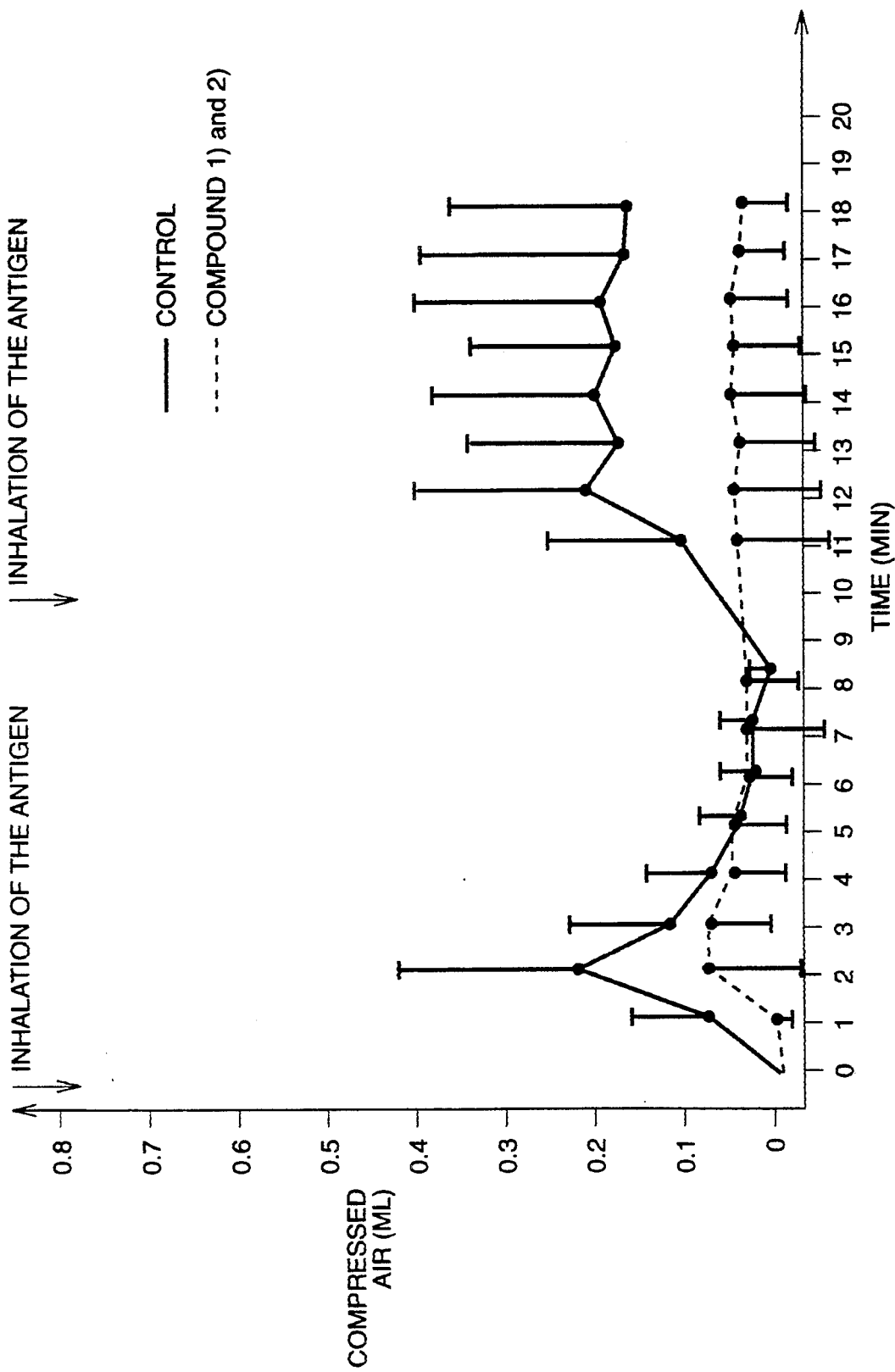

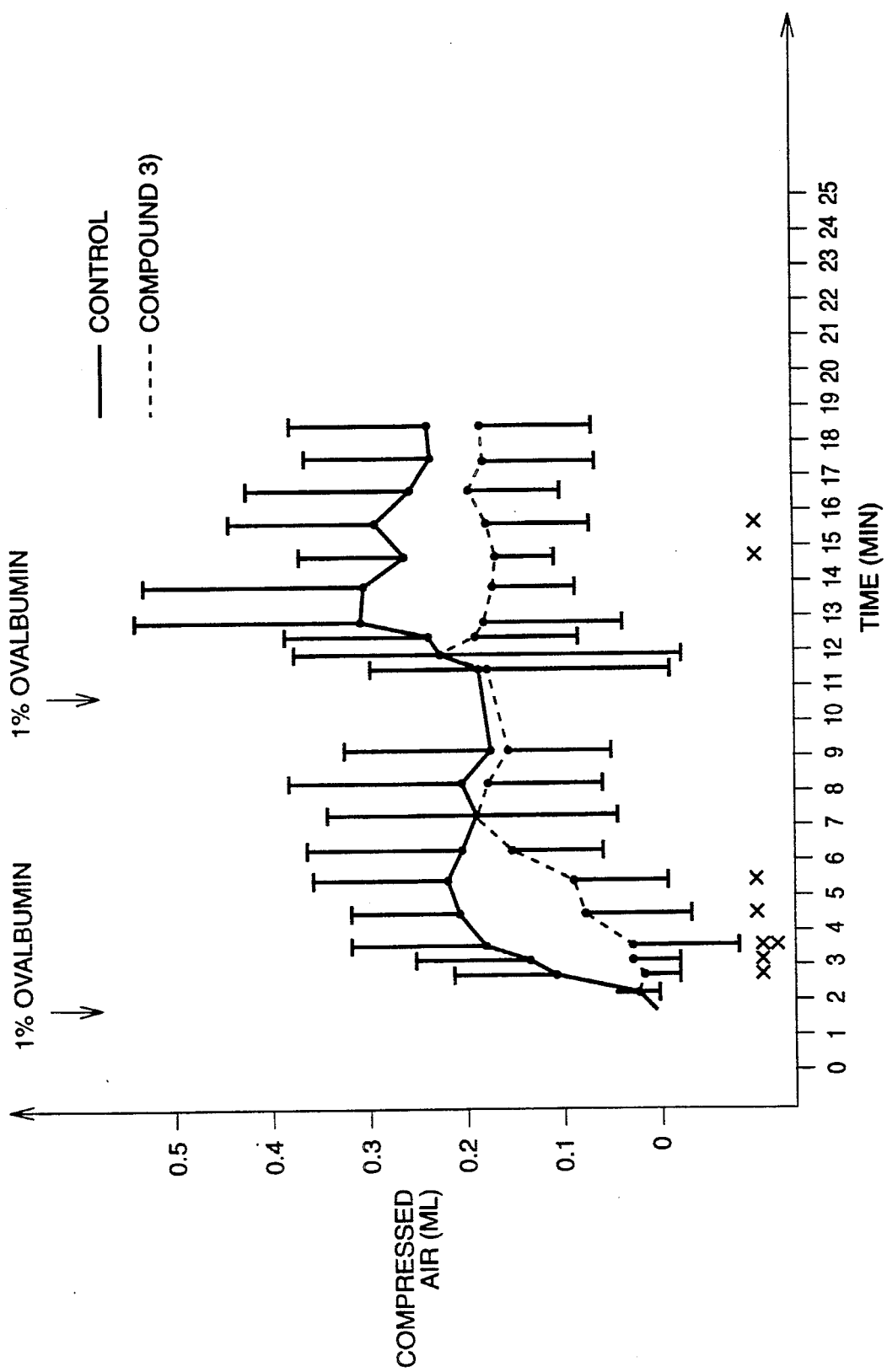

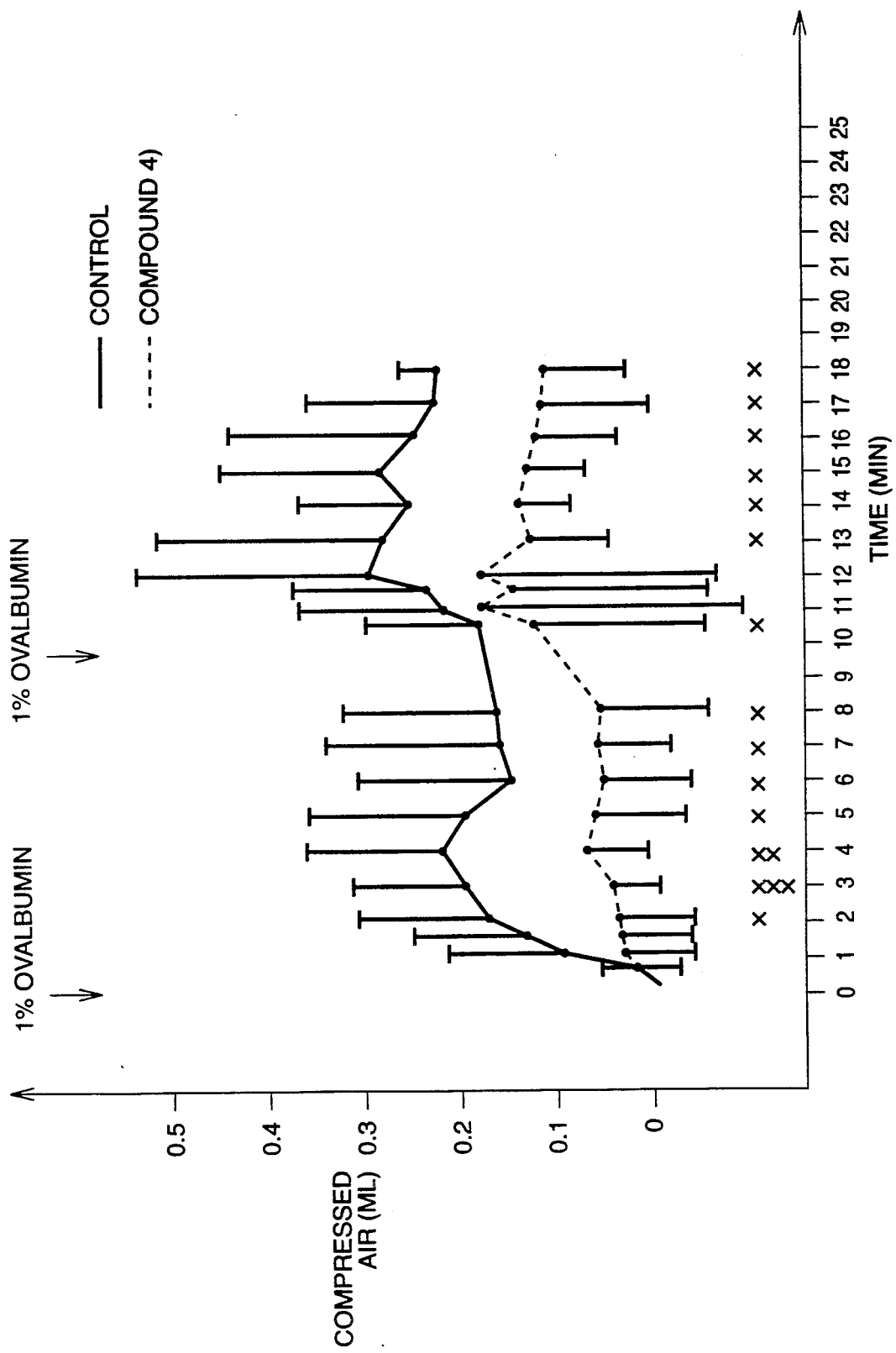

METHOD AND COMPOSITION FOR THE TREATMENT OF IMFLAMMATORY CONDITIONS USING THIOSULPHINIC ACID DERIVATIVES

BRIEF DESCRIPTION OF THE DRAWINGS

FIG. 4-6 show protective action of the compound in the case of allergen-induced asthma bronchiale of guinea pigs.

DESCRIPTION

Figure 1:
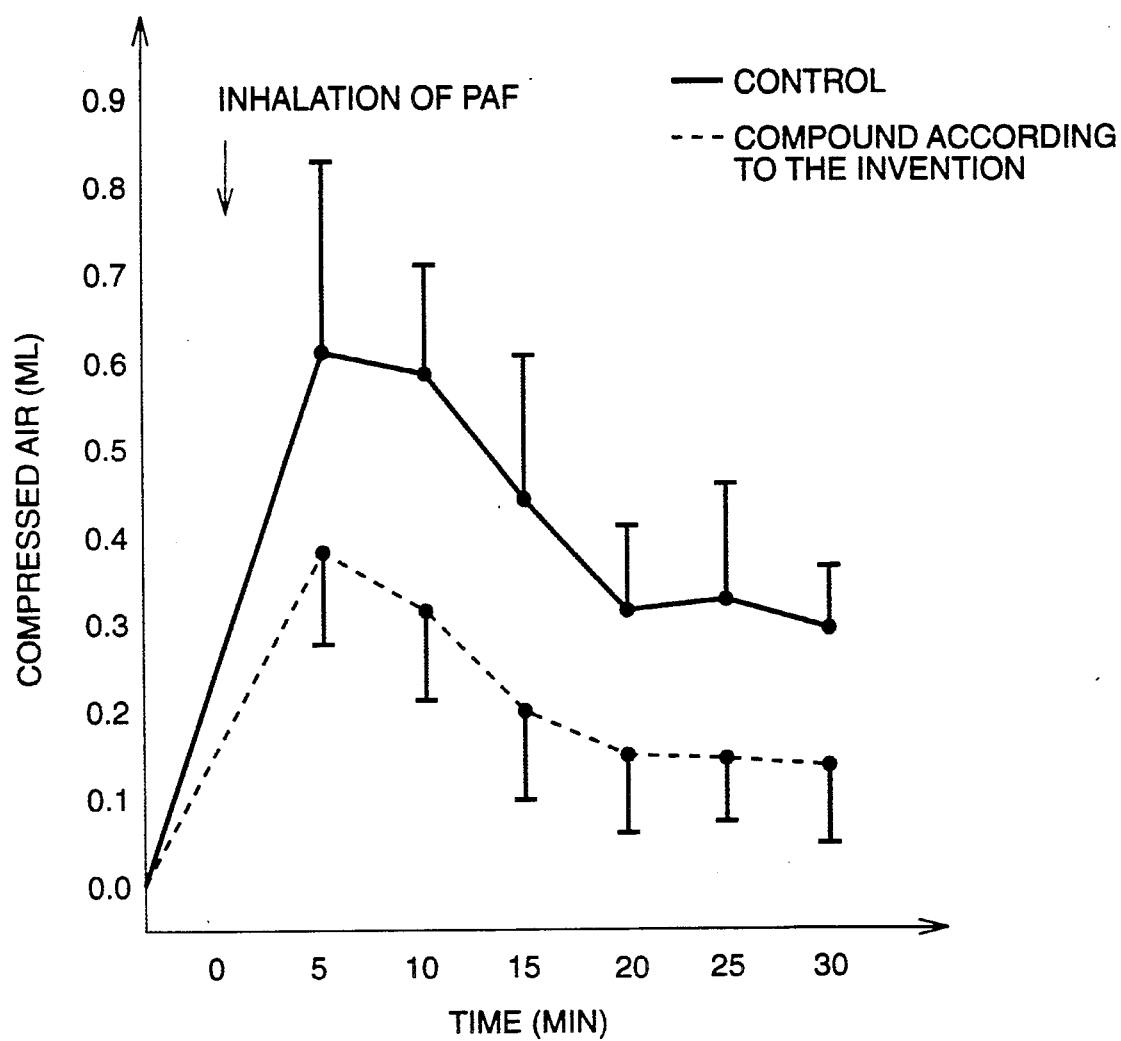
FIGS. 1-3 shows protective action of the compounds in the case of PAF-induced brochiale obstruction.

The invention concerns the use of thiosulphinic acid derivatives for the treatment of diseases in which inflammatory processes are involved in the widest sense. To these diseases belong in particular the diseases of the rheumatic type, allergic diseases, asthma, inflammations which do not belong to those above mentioned, as well as thrombotic diseases.

It is generally known that the component materials of various plants from the Liliaceae family, especially the Allium genus, possess medicinally advantageous actions. Long since known to modern medicine are the antibacterial, antimycotic and cytostatic actions of garlic; it also lowers the blood pressure, as well as the sugar and lipid level.

From U.S. Pat. No. 2,554,088, it is known that garlic extracts possess an antibiotic action and that the antibiotic action is to be attributed to the compound allyl disulphide oxide. Furthermore, from U.S. Pat. No. 2,508,745, it is known that certain thiosulphinic acid esters possess antibacterial and fungicidal actions.

It has now been found that thiosulphinic acid derivatives of the general formula I

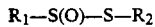

$$R_1-S(O)-S-R_2$$

in which $R_1$ and $R_2$ can be the same or different and signify a possibly singly or multiple substituted alkyl radical, aryl radical, aralkyl radical, alicyclic radical or heterocyclic radical, which can either—insofar as they are onion component materials—be extracted from the juice of pressed onions (All. cepa) or be prepared in a chemical way, display generally inflammation-inhibiting properties not only in vitro but also in vivo.

The compounds of the general formula I are, in part, new materials but in part their structure belongs to no pharmacological usefulness in the state of the art (see e.g. Rec. Trav. Chim. Pays-Bas 73, 129 (1954)). It is common to all that these compounds possess an excellent anti-asthmatic, inflammation-inhibiting, anti-allergic, analgesic and also antipyretic action. They are also suitable for the prevention of tissue rejection reactions.

Therefore, according to the invention, there are made available thiosulphinic acid derivatives of the general formula

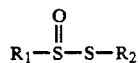

$$\underset{R_1-S-S-R_2}{\overset{O}{\parallel}} \quad (I)$$

wherein $R_1$ and $R_2$ have the above-given meanings, possibly in combination with a pharmacologically acceptable carrier, for use in the treatment or for use in the preparation of medicaments for the treatment of a disease of the above-mentioned type.

By an alkyl radical are to be understood straight-chained, branched, saturated and unsaturated alkyl radicals with 1 to 6 carbon atoms, for example a methyl, ethyl, n-propyl, isopropyl, alkyl, 1-propenyl radical, butyl, pentyl and hexyl radical. Methyl, ethyl, n-propyl, allyl and 1-propenyl radicals are especially preferred.

By an aryl radical or the aryl moiety of an aralkyl group is to be understood an aromatic hydrocarbon radical with 6 to 14 carbon atoms, for example a phenyl, naphthyl or anthryl radical, preferably a phenyl radical.

Straight-chained, branched, saturated or unsaturated alkylene radicals with 1 with 4 carbon atoms, such as methylene, ethylene, vinylene, propylene, propenylene, isopropylene, butylene or ethylethylene, form the alkylene moiety of the aralkyl groups.

The substituents possibly provided on the aryl and aralkyl radicals are preferably $C_1$ to $C_6$-alkyl, $C_1$ to $C_6$-alkoxy, $C_1$ to $C_6$-alkylthio, halogen, hydroxyl, formyl, carboxyl, amino, nitro, cyano, aryloxy, aryl, aralkyl, whereby, by halogen is understood bromine, chlorine, fluorine or iodine, preferably chlorine or fluorine, aryloxy, for example phenoxy, naphthoxy or anthryloxy, preferably phenoxy, aryl has the above-given meaning and is preferably phenyl and aralkyl has the above-given meaning and preferably signifies benzyl.

By an alicyclic radical is to be understood a possibly unsaturated cycloaliphatic group with 6 to 10 carbon atoms, e.g. a cyclohexyl, cyclopentyl or cyclohexenyl radical, preferably a cyclohexyl radical.

By a heterocyclic radical is to be understood e.g. a pyridinyl, a piperidyl, morpholinyl or tetrahydropyranyl radical. Insofar as nothing otherwise is there stated, the above-mentioned radicals can possibly be substituted by one or more of the following groups, such as e.g. hydroxyl, formyl, carboxyl, amino, cyano or halogen atoms.

For the compounds which one can isolate from pressed onion juice, it was found that $R_1=R_2$=methyl or propyl; that when $R_1$ is methyl or 1-propenyl, $R_2$ is 1-propenyl or methyl or that when $R_1$ is (propyl) or 1-propenyl, $R_2$ is 1-propenyl or propyl.

The term inflammation, as it is to be understood in the sense of the invention, is generally defined as reaction of the organism and of its tissue against various kinds of damaging irritation. By damaging irritations are to be understood exogenic and also endogenic irritations, such as e.g. tissue damages, the penetration of foreign bodies, chemical materials, bacterial toxins, allergens, immune complexes, microorganisms, morbid metabolic products, as well as breakdown products of tumours. The classical symptoms of pain and fever are closely connected with the inflammatory process.

It is long known that certain substances peculiar to the body, the so-called mediators, are closely connected with the course of the inflammation. These mediators, to which an extraordinarily great pathogenic importance is attributed, are liberated by the harmful occurrence (noxae) from the body cells. Histamine, 5-HT (5-hydroxytryptamine), bradykinin, the prostaglandins, prostacyclins, the leukotrienes, thromboxanes and the thrombocyte-activating factor (in the following referred to as PAF; Engl.: platelet activating factor), first better investigated in recent times, count as the most important and best known mediators.

These and other mediators act extraordinarily strongly on the contraction of the smooth musculature, lead to heart function disturbances, impair the integrity of blood vessels and mucous membranes, such as e.g. that of the bronchial system; furthermore, they bring about the aggregation of thrombocytes and polymorphonuclear leukocytes with the serious results of an anaphylactic contraction of the respiratory tract, blood pressure decrease, heart arrhythmias, plasma exudation, tissue oedema, haemoconcentration, thrombocytopenia, leukocytopenia, clumping of the thrombocytes and polymorphonuclear leukocytes in the lung capillaries, most severe respiratory disturbances and circulatory collapse.

On the basis of their broad pharmacological activity spectrum, their wide distribution in the organism, their formation by numerous physical, chemical, pathological, pathophysiological and pharmacological influences, as well as on the basis of their participation in the case of a plurality of pathophysiological sequences, the mediators or their pharmacological influencing are of the greatest medicinal importance (cf. The Pharmacological Basis of Therapeutics, ed., Goodman and Gilman, 6th edition, 1980, McMillan Publishing Company).

According to the invention, there is preferred the use of the thiosulphinic acid derivatives in the case of PAF-induced pathological states, for which reason, in the following, the thrombocyte-activating factor (PAF) is considered in more detail.

PAF is a glycerophosphocholine with the chemical designation 1-O-alkyl-2-acetyl-sn-glycerol-3-phosphoryl-choline. It is liberated from a number of cells, such as e.g. macrophages, basophilic and neutrophilic granulocytes and the like, as the result of an allergen-induced activation of these cells. The liberation of PAF brings about a number of the pathological conditions already described above, whereby PAF does not have to act directly but rather can manifest its action via a stimulation of further mediators. Recent investigations show, in particular, an important role of PAF in the genesis of clinical bronchial asthma, as well as in the case of other pathological conditions of the lungs, e.g. of obstructive bronchitis.

Besides its important role in the case of the genesis of bronchial asthma and in the case of anaphylaxis, PAF is to be seen as a highly potent inflammation mediator with the pathological actions already described above.

A number of the above-mentioned mediators, including PAF, are liberated by a membrane-bound phospholipase from phospholipids of the cell membrane, whereby, on the one hand, arachidonic acid and, on the other hand, a PAF precursor is formed.

Starting from arachidonic acid, two groups of mediators are formed:
 i) by the enzyme cyclooxygenase, the prostaglandins, including prostacyclin and thromboxane;
 ii) by the enzyme lipoxygenase, the open-chained hydroperoxy and hydroxy acids and especially the leukotrienes.

The PAF precursor is converted into the active compound by an acetyl transferase.

Pharmacologically important in the case of the treatment of inflammations are two groups of active substances: it is a question, on the one hand, of the so-called non-steroidal antiphlogistics, which are compounds and derivatives of salicylic acid. Further compounds with known antiphlogistic action are the pyrazolone derivatives, the para-aminophenol derivatives, the indole derivatives (e.g. indomethacin) and the derivatives of propionic acid. The pharmacological action of all of these compounds depends upon the fact that they are able to inhibit cyclooxygenase and thus suppress the synthesis of the prostaglandins or thromboxanes.

Salicylic acid or its derivatives and the further compounds of the whole class are afflicted with a series of severe and most severe side effects. Thus e.g. the long-term administration of salicylic acid derivatives leads to stomach and intestinal ulceration. Also known are the relative incompatibility of the pyrazolone derivatives, the hepatotoxic action of the para-aminophenol derivatives, the general incompatibility of indomethacin, as well as the ulcerative action of the propionic acid derivatives.

A further also serious disadvantage of the non-steroidal antiphlogistics consists in the fact that, under certain circumstances, they strengthen the pathological action of the mediators in that, due to the inhibition of cyclooxygenase, more substrate is made available for the lipoxygenase and thus for the formation of leukotrienes.

Against the non-steroidal antiphlogistics, there stand the steroidal antiphlogistics which are the corticosteroids and their derivatives. The antiphlogistic action of the corticosteroids depends upon their ability to inhibit phospholipase, as well as lipoxygenase, whereby the whole arachidonic acid metabolism is inhibited. Disadvantageous for the therapy with corticosteroids are the fatal side effects of which, only by way of example, the following are to be mentioned: ulcera duodeni or ventriculi, myopathy, osteoporoses, psychic disturbances, increased susceptibility to infection, subcapsular cataracts and the like.

Besides the corticosteroids, there are the lipoxygenase inhibitors, such as e.g. benoxaprofen. These substances are also involved with severe side effects, such as e.g. fatally proceeding exfoliative dermatitides (scalded skin syndrome).

The compounds used according to the invention inhibit not only cyclooxygenase, thromboxane synthetase, but also lipoxygenase and, furthermore, also possess the property of blocking PAF-induced effects. Therefore, they possess the properties of the steroidal antiphlogistics without, however, displaying their fatal side effects and are, therefore, valuable for the treatment of inflammatory processes in the widest sense in the causation of which the known mediators, such as e.g. prostaglandins, histamine, PAF, leukotrienes and thromboxanes, play a part.

In contradistinction to the non-steroidal antiphlogistics, which do not act against the aspects of chronic inflammatory diseases initiated by leukocytes, since they do not inhibit the leukotriene formation, the compounds here used are also in this regard superior to the known compounds because of their surprising, excellent and advantageous action.

Inflammation-inhibiting corticosteroids indirectly inhibit the production not only of the prostaglandins but also of the leukotrienes, whereby one explains at least in part their excellent therapeutic actions. As described above, the treatment with steroids is involved with serious local and also systemic side effects so that a comparatively long administration of corticosteroids is contraindicated in many inflammatory conditions.

The use according to the invention of the compounds fulfils the requirement for non-steroidal antiphlogistics of inhibiting the synthesis of leukotrienes and prostaglandins and thromboxanes and of countering the effects of PAF. They are free from the disadvantages involved with the steroidal or non-steroidal antiphlogistics.

Therefore, the compounds, as well as their pharmaceutically acceptable compositions, can be administered in small doses for the achievement of a therapeutic inflammation-inhibiting action.

The invention is further explained by the Examples given in the following:

Preferred in the sense of the present invention are, apart from the compounds mentioned in the Examples, the following: 4-bromobenzenethiosulphinic acid S-phenyl ester 4-chlorobenzenethiosulphinic acid S-phenyl ester 3-methylbenzenethiosulphinic acid S-phenyl ester 2,4-dimethylbenzenethiosulphinic acid S-phenyl ester 4-ethoxybenzenethiosulphinic acid S-phenyl ester 4-chlorobenzenethiosulphinic acid S-4-methoxyphenyl ester 3-nitrobenzenethiosulphinic acid S-4-methoxyphenyl ester 4-methylthiobenzenethiosulphinic acid S-phenyl ester 4-phenylbenzenethiosulphinic acid S-phenyl ester benzenethiosulphinic acid S-2-carboxyphenyl ester 2-phenoxybenzenethiosulphinic acid S-phenyl ester pyridine-3-thiosulphinic acid S-phenyl ester benzenethiosulphinic acid S-(2-pyridyl) ester benzenethiosulphinic acid S-(2-naphthyl) ester naphthalene-2-thiosulphinic acid S-phenyl ester benzenethiosulphinic acid S-2-aminophenyl ester benzenethiosulphinic acid S-4-hydroxyphenyl ester benzenethiosulphinic acid S-2,6-dichlorophenyl ester benzenethiosulphinic acid S-3,5-di-t.-butyl-4-hydroxyphenyl ester.

The compounds for use in the sense of the present invention can be isolated from onions, for example by the following process:

EXAMPLE 1

A) Starting material:

One obtains pressed onion juice from peeled, comminuted and homogenised onions (Allium cepa). Before the pressing, the homogenate is left to stand for at least 20 minutes. The pressed juice is extracted twice with dichloromethane, chloroform or other organic solvent not miscible with water; the organic phase is dried over sodium sulphate, filtered off and the solvent distilled off under reduced pressure. One obtains a yellowish-green oily residue.

This residue is fractionated by chromatographic processes.

B) Fractionation/method I:

1. For the coarse fractionation, there is suitable e.g. the column chromatography on silica gel with toluene-/ethyl acetate (10:3) as eluent.

2. Subsequently, a renewed column chromatographic separation of enriched fractions of the active substances on silica gel with e.g. dichloromethane/acetone (100:1) as eluent provides the compounds according to the invention.

For this separation step, elution agent systems based on chloroform or dichloromethane with admixtures of 1 to 5% of acetone, ethyl methyl ketone, diethyl ether or elution agent systems based on hydrocarbons, such as heptane, pentane or hexane with admixtures of 5 to 10% of acetone or ethyl methyl ketone are suitable.

EXAMPLE 1a

B) Fractionation/method II:

Starting from the residue of the organic extraction from pressed onion juice, the isolation of the compounds can be simplified as follows:

1. The triterpenes laying above on silica gel in part with the substances to be isolated are first separated off by "flash chromatography" on reversed-phase material (e.g. RP 8 or RP 18) with the use of a hydrophilic elution agent (e.g. methanol).

2. Thereafter, with the help of middle pressure liquid chromatography (MPLC), the isolation of the thiosulphinic acid esters is possible in one step. As stationary phase, there again serves silica gel, as eluent the solvent mixtures of the second fractionation step of Method I (see Example 1).

EXAMPLE 2

On the basis of the good solubility of the compounds in lower alcohols (e.g. methanol, ethanol), an alcohol extraction from e.g. lyophilised onion homogenate, is also possible. Subsequently, one can fractionate according to method I (Example 1) or II (Example 1a).

EXAMPLE 3

Extraction:

The pressed onion juice is extracted with organic solvents which are not miscible with water, such as e.g.: dichloromethane, chloroform, diethyl ether and further solvents of comparable polarity. Organic solvents of very low polarity, such as e.g. petroleum ether, are not suitable.

EXAMPLE 4

The juice or also the homogenate can also be extracted with supercritical gases, such as e.g. $CO_2$, under pressure.

According to each of the above Examples, in each case one obtains six thiosulphinic acid derivatives with the following formula:

(II)

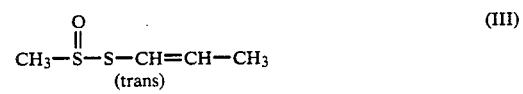
(trans) (III)

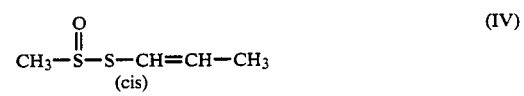
(cis) (IV)

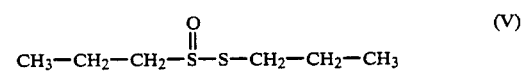
(V)

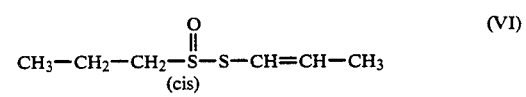
(cis) (VI)

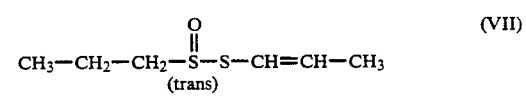
(trans) (VII)

Under certain circumstances, the structures of compounds VI and VII are to be assigned transposed.

The storage of the extracts, fractions and pure substances takes place with the exclusion of light and oxygen at $-20°$ C.

Chromatographic characterisation of the thiosulphinic acid esters isolated from onions.

1) Thin layer chromatography:

a) Stationary phase: HPTLC finished plates silica gel 60F 254, layer thickness 0.25 mm.

| b) Mobile phase | compound | $R_f$ value |
|---|---|---|
| toluene/ethyl acetate (10:3) | II | 0.25 |
|  | III | 0.31 |
|  | IV | 0.35 |
|  | V | 0.44 |
|  | VI | 0.46 |
|  | VII | 0.50 |
| chloroform/acetone (100:4) | II | 0.47 |
|  | III | 0.49 |
|  | IV | 0.49 |
|  | V | 0.54 |
|  | VI | 0.57 |
|  | VII | 0.57 |
| dichloromethane/acetone (100:1) | II | 0.28 |
|  | III | 0.34 |
|  | IV | 0.38 |
|  | V | 0.37 |
|  | VI | 0.40 |
|  | VII | 0.44 | c) UV behaviour

All thiosulphinic acid esters show a distinct fluorescence reduction in UV 254.

d) Detection behaviour:

| spray reagent | compound | reaction |
|---|---|---|
| ethanolic sulphuric acid | II | none |
| 5%/vanillin | III | weak brown-red |
| (1% in EtOH) 110° C. | IV | " |
|  | V | none |
|  | VI | weak reddish |
|  | VII | " |
| palladium (II) chloride | II | yellow-brown |
| solution 1% in water | III | brown |
|  | IV | brown |
|  | V | bright yellow |
|  | VI | brown |
|  | VII | brown |
| 5% sodium nitroprussite | II | bright red |
| sodium in water/ethanolic | III | " |
| sodium hydroxide solution (10%) | IV | " |
|  | V | " |
|  | VI | " |
|  | VII | " |

2) High pressure liquid chromatography
 a) Stationary phase: Hibar finished column RT 125-4; Lichrospher 100 CH-18/2, 5 um.
 b) Mobile phase: acetonitrile/water gradient system
 c) Detection at 200 nm
 d) Retention times:
 In the case of use of a gradient system from 20% to 80% acetonitrile in 30 min. there are given retention times of 1.80 min. (compound II), 4.25 min. (compound III), 4.40 min. (compound IV), 10.19 min. (compound V), 9.97 rain. Compound VI ) and 10.19 rain. (compound VII).

Furthermore, the compounds can be prepared in a chemical way according to per se known processes for the preparation of analogous compounds:

EXAMPLE 5

Benzenethiosulphinic acid S-phenyl ester.

To a solution of 2.2 g. (20 mmol) thiophenol in 30 ml. dry ether one adds 1.8 g. pyridine and adds dropwise thereto, with cooling, a solution of 3.2 g. (20 mmol) benzenesulphinic acid chloride in 20 ml. dry ether. One allows to stir further for 10 min., pours into dil. sulphuric acid, separates off the organic phase, dries and evaporates. There remain 3.2 g. of the title compound (68% of theory) of the m.p. 69°–70° C. (from ligroin).

EXAMPLE 6

In a way analogous to that described in Example 5, one obtains:

| designation | yield % | melting point °C. |
|---|---|---|
| a) benzenethiosulphinic acid S-4-methylphenyl ester | 81 | 68 |
| b) 4-methylbenzenethiosulphinic acid S-phenyl ester | 71 | 70–71 |
| c) 4-methylbenzenethiosulphinic acid S-4-methylphenyl ester | 86 | 86 |
| d) benzenethiosulphinic acid S-4-t.-butylphenyl ester | 81 | 70 |
| e) 4-t.-butylbenzenethiosulphinic acid S-phenyl ester | 81 | 80–81 |
| f) 4-t.-butylbenzenethiosulphinic acid S-4-t.-butylphenyl ester | 74 | 104–105 |
| g) benzenethiosulphinic acid S-4-methoxyphenyl ester | 68 | 75–77 |
| h) 4-methoxybenzenethiosulphinic acid S-phenyl ester | 72 | 61–62 |
| i) 4-methoxybenzenethiosulphinic acid S-4-methoxyphenyl ester | 91 | 90–91 |
| j) 4-methylbenzenethiosulphinic acid S-4-methoxyphenyl ester | 75 | 79 |
| k) 4-methoxybenzenethiosulphinic acid S-4-methylphenyl ester | 90 | 83 |
| l) 4-methylbenzenethiosulphinic acid S-4-chlorophenyl ester | 77 | 92–93 |

EXAMPLE 7

One obtains thiosulphinic acid derivatives in which $R_1$ and $R_2$ have the same meaning analogously to Kametani et al., Jap. J. Pharm. Chem. 31 (1959), p. 60 and Bailey et al. J. Am. Chem. Soc.—69, (1947), p. 1712 by oxidation of the corresponding disulphides with an equimolar amount of 3-chloroperbenzoic acid (or perbenzoic acid or peracetic acid) at 0° C. in dichloromethane (or trichloromethane or acetic acid).

0.05 mol dipropyl sulphide are dissolved in 300 ml. dichloromethane and the solution cooled in an ice-bath. With the help of a separating funnel, 0.045 mol 3-chloroperbenzoic acid, dissolved in 75 ml. dichloromethane, are slowly added dropwise, with stirring. Thereafter, it is stirred for a further 15 min. and the precipitate filtered off. After washing with, in each case, 300 ml. 5% NaHCO$_3$ solution, 3% NaHCO$_3$ solution an aqua dem., the organic phase is dried over Na$_2$SO$_4$ and the solvent stripped off under reduced pressure.

The purification from by-products and non-reacted dipropyl sulphide took place by means of Chromatotron or flash chromatography on silica gel: Non-reacted dipropyl sulphide is thereby first eluted with n-hexane, thereafter propylthiosulphinic acid propyl ester and propylthiosulphonic acid propyl ester separated with dichloromethane:acetone (100:1). The identification of the oily substance takes place by ultra-violet spectroscopy ($_{max}$=240 nm (diode array) and HPLC chromatography Rt: 9.9 min.

For the high pressure liquid chromatography (HPLC), there is used reversed phase material with acetonitrile/water gradient elution. In order to include substances without chromophoric groups, detection is at 200 nm.

In a universal system for all worked sulphur-containing compounds, the acetonitrile concentration increases in 30 min. linearly from 20% to 80%.

The yield amounts to 65% of theory.

EXAMPLE 8

In a way analogous to Example 7, there are obtained
a) from dimethyl disulphide, methylthiosulphinic acid methyl ester
 yield: 50% of theory
 M.p.: colourless, very mobile oil
 Rt: 1.7 rain. ( HPLC )
 UV: $_{max}=240$ nm (diode array)
 (The separation of the thiosulphinic acid ester from thiosulphonic acid ester takes place in the elution agent system dichloromethane/acetone (100:2));
b) from diallyl disulphide, allyl thiosulphinic acid allyl ester
 Yield: 10% of theory
 M.p.: oil
 Rt: 12.3 min. (HPLC)
 UV: $_{max}=260$ nm (diode array)
 Elution agent system: dichloromethane/acetone (100:1); and
c) from diphenyl disulphide, phenylthiosulphinic acid phenyl ester
 Yield: 75% of theory
 M.p.: 62°=63° C.
 Rt: 18.4 rain. (HPLC)
 UV: $_{max}=222, 283$ nm (diode array)
 Elution agent system: dichloromethane/n-hexane (1:1).

EXAMPLE 9

Methylthiosulphinic acid phenyl ester and phenylsulphinic acid methyl ester 0.2 mol thiophenol, together with 0.2 mol dimethyl disulphide, are dissolved in 500 ml. methanol with the addition of 80 ml. 1% methanolic KOH and 10 ml. water.

The reaction batch is heated to the boil under reflux for 3 h. in a fume cupboard until the HPLC investigation shows the absence of dimethyl sulphide.

Subsequently, the methanolic solution is mixed with 300 ml. of water and extracted 3x with 500 ml. n-pentane. The pentane phase is dried and the solvent distilled off.

The disulphides obtained are then oxidised as in Example 7 and the batch worked up correspondingly. The obtaining of the pure thiosulphinates takes place by middle pressure liquid chromatography (MPLC) on silica gel with dichloromethane as elution agent.

I) Methylthiosulphinic acid phenyl ester
 Oil
 Rt: 7.8 rain. (HPLC)
 UV: $_{max}=223$ (sh), 250 nm (diode array)
II) Phenylthiosulphinic acid methyl ester
 Oil
 Rt: 9.2 min. (HPLC)
 UV: $_{max}=220$ (sh), 260 nm (diode array)

EXAMPLE 10 n-Propylthiosulphinic acid methyl ester and methylthiosulphinic acid n-propyl ester In an analogous way as in Example 9, from propanethiol and dimethyl disulphide are prepared the two title compounds.

EXAMPLE 11

The thiosulphinates isolated from Allium cepa L. are also accessible by incubation of synthesised (+)-alk(en)yl-L-cysteine sulphoxides with an alliinase preparation under suitable conditions.

EXAMPLE 12

Finally, the compounds can also be prepared starting from sulphinic acid chlorides and thiols as described by T. L. Moore, D. E. O'Connor for analogous compounds (J. Org. Chemistry, 31 (1966), p. 3587.

According to the invention, the compounds can be used for the treatment of inflammations of the joints, of the skin, of the mucous membranes, as well as of internal organs, regardless of whether these have been brought about by infection pathogens, immunological processes or trauma. Inflammatory processes of the bronchial system, such as asthma bronchiale or obstructive bronchitis, are hereby indications which are especially advantageous to treat. Furthermore, the compounds can be used for the prophylaxis and treatment of blood vessel and heart diseases in which it appears to be desirable to prevent the biosynthesis of inflammatory materials by thrombocytes. The compounds can be used especially advantageously for the prophylaxis or treatment of all PAF- and/or leukotriene-induced phenomena and especially for the treatment of the bronchial area.

Furthermore, according to the present invention, a compound of the general formula (I) is made available for use in a process for the inhibiting of lipoxygenase, cyclooxygenase and thromboxane synthetase in a mammal, for example the human. Furthermore, the invention makes available the use of a compound for the treatment or prophylaxis of a mammal, including humans, especially for the treatment of one of the previously described illnesses or conditions.

The necessary amount of the compound to be used (in the following characterised as the active component) for the therapeutic action depends upon the particular compound, the mode of administration and upon the subject to be treated, as well as upon the particular illness. A suitable dosage of a compound for administration to a mammal which suffers frown an inflammation, a painful or feverous state as previously described amounts to about 0.1 µg. to 500 mg. of the active component per kilogram of body weight. In the case of a systemic administration, the dosage can be in the range of 0.5 to 500 mg. of the active compound per kilogram body weight and the most preferred dosage in the range of 0.5 to 50 mg. per kilogram body weight, for example 5 to 25 mg. per kilogram body weight, which is administered two or three times daily.

In the case of a topical administration, e.g. to the skin or mucous membrane, the suitable dosage can lie distinctly higher.

Although it is possible to administer the active component alone, it is preferred that this is administered in the form of a pharmaceutical formulation which contains a compound according to the general formula and a carrier material acceptable therefor. Usually, the active component is present in such a formulation in a concentration of 0.1 to 99.9 wt. % of the formulation. Usually, a single dosage of a formulation contains between 0.1 mg. and 1 g. of the active component. For the topical administration, the concentration of the active component preferably amounts to 1to 2 wt. % of the composition but the active component can account for up to 10 wt. %. Compositions which are suitable for a nasal or buccal administration, such as e.g. self-atomising powder, can contain 0.1 to 20 wt. %, e.g. 2 wt. % of the active component.

The compositions for the use according to the invention in veterinary as well as in human medicine contain the active component in combination with a carrier material pharmaceutically acceptable therefor and possibly further therapeutically active components. The carrier material must be acceptable in the sense that it is compatible with the other components of the formulation and possesses no disadvantageous action on the recipient of the formulation.

The compositions are suitably present in the form of an oral, opththalmological, rectal, parenteral (including subcutaneous, intramuscular and intravenous), intra-articular, topical, nasal or buccal form of administration.

The formulations are usually present in the form of a single dose and can be produced by any process known in the field of pharmaceutical technology. All processes contain the step of the bringing together of the active component with the carrier material, possibly with one or more additional components. In general, the compositions are prepared by uniform and intimate mixing of the active component with a liquid carrier or a finely divided solid carrier or both and subsequently, if necessary, forming of the product into the desired form of administration.

The compositions according to the invention for oral administration can be present in the form of discrete units, such as for example capsules, cachets, tablets or pastilles, whereby each form contains a predetermined amount of the active component. They can also be present in the form of a powder or in the form of granules or in the form of a solution or suspension in an aqueous or non-aqueous liquid or in the form of an oil-in-water emulsion or water-in-oil emulsion. The active component can also be present in the form of a bolus, of an electuary or of a paste.

One can produce a tablet which contains the compound by pressing or casting of the active component possibly together with one or more additional components. One can produce pressed tablets by pressing of the active component in free flowing form, e.g. as powder or as granules, possibly admixed with a binding agent, a lubricant, an inert dilution agent, surface-active or a dispersion agent in a suitable machine. One can produce cast tablets by casting of a mixture of the active component present in powder form and of a suitable carrier material which is moistened with an inert liquid dilution agent in a suitable machine.

The formulations for rectal administration can be present in the form of suppositories, whereby the active component is present in a carrier, e.g. of cocoa butter, but they can also be present in the form of an enema.

The compositions suitable for parenteral administration usually contain a sterile aqueous composition of the active component which is advantageously isotonic with the blood of the recipient.

Compositions which are suitable for intraarticular administration can be present in the form of a sterile aqueous composition of the active component, whereby the active component is possibly present in micro-crystalline form, e.g. in the form of an aqueous micro-crystalline suspension. In the same way, liposomal compositions or biodegradable polymer systems can be used for the administration of the active component.

Compositions suitable for topic administration contain liquid or semi-liquid compositions, such as e.g. embrocations, lotions, dressings, oil-in-water or water-in-oil emulsions, such as e.g. creams, salves or pastes, or solutions or suspensions, such as e.g. drops, For example, the active component for ophthalmological administration can be present in the form of aqueous eye drops, for example in the form of a 0.1 to 1.0% solution.

Compositions suitable for the administration through the nose or into the buccal cavity are present in the form of a self-atomising powder or in the form of spray compositions, such as e.g. aerosols. After dispersion, the composition gives a particle size in the range of 10 to 200 $\mu$m.

Compositions which are used according to the present invention can also contain the active component in an aqueous or dilute alcoholic solution. The active component can possibly be converted by a spray device into a fine mist which is inhaled by patients. Such compositions usually contain a flavouring agent, such as e.g. sodium saccharin and an ethereal oil. There can also be contained a buffer substance and/or a surface-active agent in such compositions, together with a preserving agent, such as e.g. methyl hydroxybenzoate.

Other compositions which are suitable for administration through the nose consist of a coarse powder which has a particle size of 20 to 500 $\mu$m. which is administered in the same way as snuff.

In addition to the above-mentioned components, the compositions for use according to the invention can contain one or more additional components, such as dilution agents, buffer substances, flavouring materials, binding agents, surface-active agents, thickening agents, lubricants, preserving agents, e.g. methyl hydroxybenzoate (including anti-oxidants), emulsifying agents and the like.

Subsequently, the action of the compounds of the general formula (I) is indicated on the basis of in vitro and in vivo experiments.

1. Investigation of the asthma-protective action of compounds in vivo. There was used a mixture of compounds 1) (identical with formula III on p.13 of the German text) and compound 2) (identical with formula IV on p.13 of the German text). The ratio of 1): 2) amounted to about 1:2.

For the investigation of the asthma-protective action in vivo, corresponding experiments were carried out with guinea pigs (Dorsch W. et al., Pflügers Arch. 391, page 263 (1981).

a) Protective action in the case of PAF-induced bronchial obstruction.

Corresponding to a randomised crossover protocol, 7 guinea pigs were either fed with the active component in olive oil or they received the carrier material olive oil alone. The dosage of the active component amounted to 20 mg. per kg. body weight. 30 min. later, the animals inhaled 10 $\mu$g. PAF. The resulting bronchial obstruction was determined whole body plethysmo-graphically in 5 min. intervals for a period of 30 min. (as measure of the bronchial obstruction, the parameter "compressed air" is used).

The results are shown in the following Table, as well as in FIG. 1.

TABLE I

Asthmatic reactions of guinea pigs (0.1 ml. compressed air) to the inhalation of PAF

| animal | control | | | | | | | cmpd. (20 mg/kg oral) | | | | | | |
|---|---|---|---|---|---|---|---|---|---|---|---|---|---|---|
| | 0' | 5' | 10' | 15' | 20' | 25' | 30' | 0' | 5' | 10' | 15' | 20' | 25' | 30' |
| 1 | 0 | 5 | 5 | 3 | 3 | 3 | 3 | 0 | 4 | 2 | 0 | 1 | 1 | 1 |
| 3 | 0 | 6 | 8 | 6 | 3 | 3 | 3 | 0 | 3 | 3 | 1 | 1 | 1 | 1 |
| 4 | 0 | 2 | 7 | 6 | 4 | 4 | 4 | 0 | 5 | 3 | 2 | 0 | 1 | 1 |
| 5 | 0 | 6 | 5 | 3 | 1 | 1 | 2 | 0 | 4 | 4 | 4 | 3 | 3 | 3 |
| (resuscitation necessary) | | | | | | | | | | | | | | |
| 6 | 0 | 7 | 6 | 4 | 4 | 4 | 2 | 0 | 6 | 5 | 3 | 0 | 1 | 0 |
| 7 | 0 | 12 | 5 | 2 | 3 | 2 | 1 | 0 | 3 | 4 | 3 | 3 | 3 | 2 |
| 8 | 0 | 6 | 6 | 6 | 3 | 5 | 3 | 0 | 6 | 2 | 2 | 2 | 1 | 1 |
| (resuscitation necessary) | | | | | | | | | | | | | | |

Figure 2:
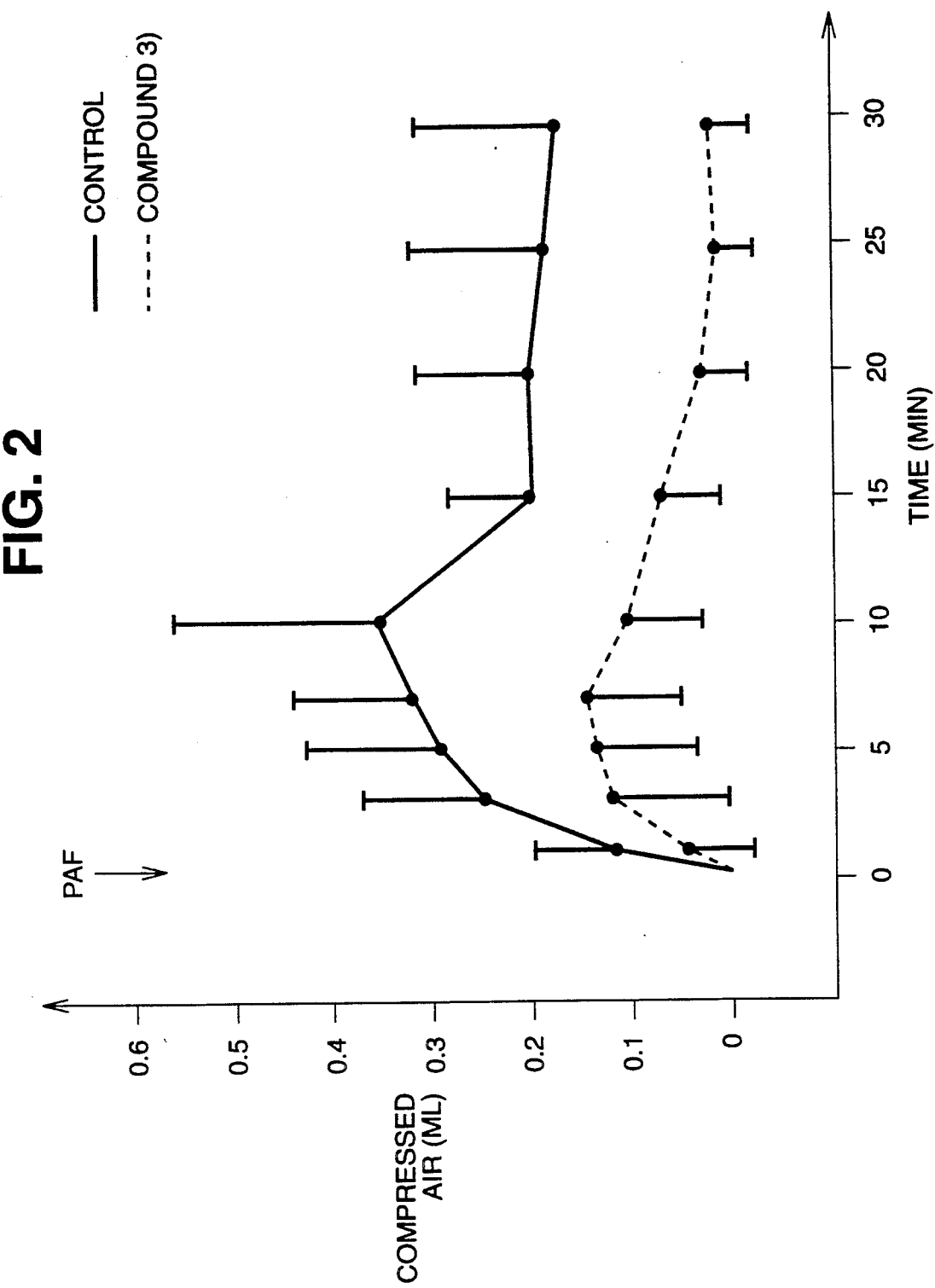
Figure 3:
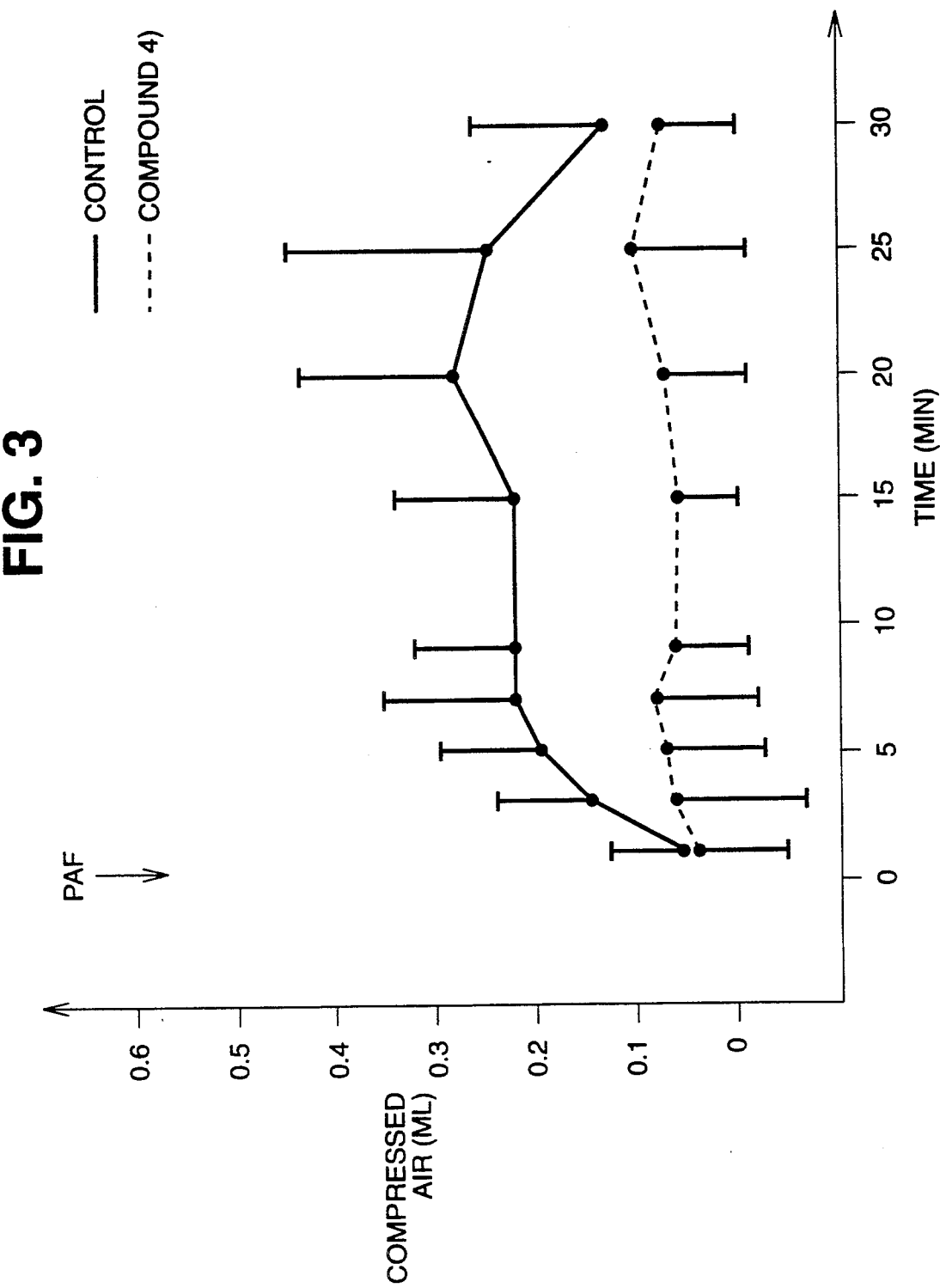

In further experiments, instead of the mixture of compound 1) and 2), compounds were used wherein $R_1$ and $R_2$ is $CH_3$ (compound 3, cf. Example 8a) or wherein $R_1$ and $R_2$ is phenyl (compound 4, cf. Example 8c). The results are shown in FIG. 2 and FIG. 3, respectively. In the case of compound 3), the dosage amounted to 50 mg./kg. and in the case of compound 4) to 100 mg./kg.

From the Table as well as from FIG. 1 to 3, one can, without difficulty, see that in the case of the animals treated with the compounds, the action of the administered PAF is substantially weaker than in the case of the control animals (larger numbers mean severe asthma). The difference was statistically significant: FIG. 1; 5 min. after inhalation $p<0.02$, 10 min. $p<0.001$ (t-test according to Student for paired data).

b) Protective action in the case of allergen-induced asthma bronchiale of guinea pigs.

9 guinea pigs were—was described under 1a)—corresponding to a randomised crossover protocol, either fed with the active component in olive oil or with the carrier olive oil alone. The dosage of the administered compound amounted to 20 mg./kg. body weight. 30 Minutes later, the animals inhaled twice, at an interval of 10 minutes, in each case for 20 seconds, a one percent ovalbumin solution, the substance to which they had been sensitised 3 weeks previously. The extent of the resulting bronchial obstruction was also determined whole body plethysmographically in 2 minute intervals for the period of twice 10 minutes (for the method see: Dorsch W, Walter O., Rosmanith J.: Continuous Recording of Intrapulmonary "Compressed Air" as a Sensitive Noninvasive Method of Measuring Branchial Obstruction in Guinea Pigs, Pflügers Arch. 391: 236–241 (1981)).

The result of this experiment is shown in FIG. 4 for the mixture of compounds 1) and 2) and in FIGS. 5 and 6 for the compounds 3) and 4) respectively. Administered dosage as in 1a). From the Figures, it follows that the administered substances clearly weaken the asthmatic reaction of guinea pigs to the inhalation of an antigen ($p<0.05$, $p<0.05$ in the case of the comparison of the maxima and minima of the asthmatic reaction; FIG. 4; t-test according to Student for paired data).

2. Investigation of the enzyme-inhibiting action of the compounds in vitro.

The enzyme-inhibiting action of the compounds were determined in vitro; use of the mixture of compounds 1) and 2).

a) Inhibition of the thromboxane biosynthesis of thrombin-stimulated platelet-rich plasma.

From a human donor was obtained platelet-rich plasma by the usual method and adjusted to a platelet count of 90,000/ml. This plasma was incubated either with a solvent (1% dimethyl sulphoxide (DMSO) -physiological common salt solution) or with various concentrations of the compounds (s. Table II).

TABLE II

| | concentration of the compounds (mg/ml) | | | | |
|---|---|---|---|---|---|
| | 0.0 | 0.001 | 0.01 | 0.1 | 1.0 |
| | thromboxane $B_2$ content in the supernatant of platelet-rich plasma (pg/ml) | | | | |
| total amount of thrombin (IU) | 0 | 280 | | | |
| | 1 | 2400 | 3400 | 3300 | 1200 | 618 |
| | 10 | 15900 | 14500 | 8600 | 2500 | 828 |

Table II: Influence of the compound on the biosynthesis of thromboxane $B_2$ in human blood platelets (pg./ml. platelet-rich plasma = pg./90000 platelets).

5 Minutes later, the platelets were stimulated with thrombin (1 or 10 International Units=I.U.) at 37° C. After 15 minutes, the reaction was stopped with ice-cold methanol (volume ratio 1:1), thereafter separated by 10 minutes centrifuging at 3000 U/min. (4° C.). Thromboxane $B_2$ was determined radioimmuno-logically in the supernatant according to the usual method; Table II shows the result of this investigation. It follows from it that the compounds inhibit the biosynthesis of thromboxane in thrombin-stimulated human platelets dependent upon concentration.

In the case of the use of 0.001 mg./ml. to 1.0 mg./ml. of compound 3) or compound 4), one finds a dosage-dependent suppression of the thromboxane $B_2$ biosynthesis of thrombin-stimulated platelet-rich plasma of maximum 61% (compound 3) and 76% (compound 4), respectively.

b) Inhibition of the 5-lipoxygenase activity of isolated pig leukocytes. Use of the mixture of compound 1) and 2).

Pig leukocytes correspond in their biochemical activity to human leukocytes, i.e. from the described investigation results, direct conclusions can be drawn to the inhibitory activity of the compounds on human granulocytes. From arachidonic acid, the enzyme 5-lipoxygenase synthesises highly potent inflammatory materials, namely, the leukotrienes $LTB_4$, $LTC_4$ and $LTD_4$.

Whole blood from pigs was made non-coagulatable by means of heparin and Na citrate, thereafter the leukocytes isolated by dextran sedimentation. After lysis of contaminating erythrocytes by hypertonic ammonium chloride solution and repeated washing, the cell count was adjusted to $4 \times 10^7$ cells per ml. of phosphate buffer (pH 7.4). By means of the addition of 10 μmol eicosatetraynic acid (ETYA), the 12-lipoxygenase was selectively blocked. The compounds to be investigated were dissolved in maximum 2% ethanolic solution and added to the cell suspensions in the following concentrations: 5, 10, 20 and 30 μmol.

Immediately thereafter, the cells were stimulated for 5 minutes at 37° C. by the addition of calcium ionophore (A 23187, 15 μmol) and radioactive-labelled arachidonic acid ($^{14}C$-arachidonic acid, 0.7 μmol=0.1 μCi).

The reaction is stopped by 1% formic acid, the supernatant of the cells extracted with $2 \times 4$ ml. ethyl acetate and then separated by means of high pressure liquid chromatography. Table III shows the result of this experiment:

TABLE III

| inhibition of the 5-lipoxygenase activity (% inhibition) | concentration of the compounds | | | | | | |
|---|---|---|---|---|---|---|---|
| | 0 | 1 | 2.5 | 5 | 10 | 20 | 30 μmol |
| | 0 | 24 | 40 | 100 | 100 | 100 | 100 |

As Table III shows, concentrations of the compounds above 5 μM inhibit the lipoxygenase of pig leukocytes 100%. The formation of leukotrienes is thus fully inhibited.

Apart frown the compounds mentioned in the Examples, the subject of the present invention are, in particular, all substances which display every possible combination of the substituents mentioned in the Examples.

We claim:

1. A method for the treatment of inflammation comprising administering to patients with inflammation a pharmaceutically effective amount of a thiosulphinic acid compound of the formula (I)

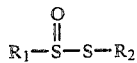

wherein $R_1$ and $R_2$, which can be the same or different, comprise an unsubstituted or substituted $C_1$-$C_6$ alkyl, $C_6$-$C_{14}$ aryl, aralkyl having a $C_6$-$C_{14}$ aryl moiety and a $C_1$-$C_4$ alkylene moiety or a $C_6$-$C_{10}$ cycloaliphatic in a pharmaceutically acceptable carrier with the proviso that when $R_1$ is $CH_3$, ethyl, propyl, butyl, amyl, allyl, benzyl, β-carboxythyl, cyclohexyl, m-carboxyphenyl, p-aminophenyl, δ-diethylaminopropyl or α-dimethyl-beta-amino-beta carboxyethyl then $R_2$ cannot be the same group, and when $R_1$ is ethane $R_2$ cannot be tert-butyl.

2. The method of claim 1 further comprising administering to patients having an inflammation the compound of formula I wherein $R_1$ or $R_2$ is an unsubstituted or substituted $C_1$-$C_6$ alkyl, phenyl, naphthyl, anthryl, benzyl, phenethyl, cyclohexyl or cyclopentyl group and wherein the substituents thereon are hydroxyl, formyl, carboxyl, amino, cyano or halogen and wherein further substituents on the phenyl, naphthyl, benzyl, phenethyl or anthryl group are $C_1$-$C_6$ alkyl, $C_1$-$C_6$ alkoxy, $C_1$-$C_6$ alkylthio, aryloxy, aryl or aralkyl.

3. The method of claim 1 or 2 further comprising administering to patients having an inflammation the compound of formula I wherein when $R_1$ is the same as $R_2$ and is methyl $R_2$ is propyl and when $R_1$ is propyl $R_2$ is methyl.

4. The method of claim 1 or 2 further comprising administering to patients having an inflammation the compound of formula I wherein $R_1$ is methyl or 1-propenyl and $R_2$ is 1-propenyl or methyl.

5. The method of claim 1 or 2 further comprising administering to patients having an inflammation the compound of Formula I wherein $R_1$ is propyl or 1-propenyl and $R_2$ is 1-propenyl or propyl.

6. The method of claim 1 or 2 further comprising administering to patients having an inflammation the compound of Formula I wherein $R_1$ or $R_2$ is unsubstituted or substituted phenyl.

7. The method of claim 1 or 2 further comprising administering to patients having an inflammation one or more of a compound selected from the group consisting of

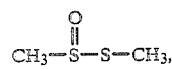 (II)

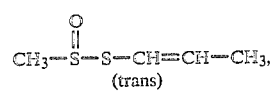
(trans) (III)

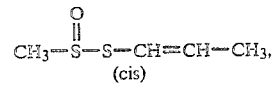
(cis) (IV)

 (V)

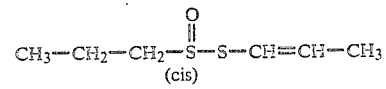
(cis) (VI)

and

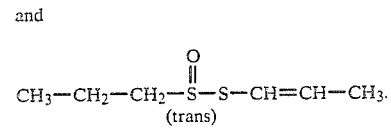
(trans) (VII)

8. The method of claim 7 further comprising administering to patients having bronchial asthma.

9. The method of claim 7 further comprising administering to patients having an allergic disease comprising allergic inflammation or allergic reactions.

10. The method of claim 7 wherein the compound acts as a lipoxygenase or cyclooxygenase inhibitor.

11. The method of claim 7 further comprising administering to patients having a PAF-induced inflammatory disease.

12. The method of claim 7 further comprising administering to a patient having rheumatism.

13. The method of claim 12 further comprising administering to a patient having polyarthritis.

* * * * *